(12) United States Patent
Kim et al.

(10) Patent No.: US 12,410,214 B2
(45) Date of Patent: Sep. 9, 2025

(54) STRUCTURALLY MODIFIED CHIMERIC POLYPEPTIDE OF HUMAN PAPILLOMAVIRUS, RECOMBINANT PROTEIN COMPRISING SAME POLYPEPTIDE, AND USE OF SAME PROTEIN

(71) Applicant: GENEMATRIX, INC., Seongnam-si (KR)

(72) Inventors: Soo Ok Kim, Seoul (KR); Suk Joon Kim, Seongnam-si (KR); Sun Pyo Hong, Seoul (KR); Jin Kim, Seoul (KR); Sang Hyun Lee, Seongnam-si (KR); Sun Ok Jang, Seoul (KR)

(73) Assignee: GENEMATRIX, INC., Seongnam-si (KR)

( * ) Notice: Subject to any disclaimer, the term of this patent is extended or adjusted under 35 U.S.C. 154(b) by 531 days.

(21) Appl. No.: 17/924,177

(22) PCT Filed: May 14, 2021

(86) PCT No.: PCT/KR2021/006075
§ 371 (c)(1),
(2) Date: Nov. 9, 2022

(87) PCT Pub. No.: WO2021/241928
PCT Pub. Date: Dec. 2, 2021

(65) Prior Publication Data
US 2023/0174589 A1    Jun. 8, 2023

(30) Foreign Application Priority Data

May 25, 2020   (KR) .................. 10-2020-0062519
May 7, 2021    (KR) .................. 10-2021-0059219

(51) Int. Cl.
| C07K 14/005 | (2006.01) |
| A61K 38/00  | (2006.01) |
| A61P 31/12  | (2006.01) |
| A61P 35/00  | (2006.01) |
| C07K 14/195 | (2006.01) |
| C07K 14/225 | (2006.01) |
| C07K 14/28  | (2006.01) |
| C07K 14/47  | (2006.01) |

(52) U.S. Cl.
CPC .......... *C07K 14/005* (2013.01); *C07K 14/195* (2013.01); *C07K 14/28* (2013.01); *C07K 14/4702* (2013.01); *C07K 2319/00* (2013.01); *C12N 2710/20022* (2013.01); *C12N 2710/20034* (2013.01)

(58) Field of Classification Search
None
See application file for complete search history.

(56) References Cited

PUBLICATIONS

Wieking et al. (A Non-oncogenic HPV 16 E6/E7 Vaccine Enhances Treatment of HPV Expressing Tumors, Cancer Gene Ther. Oct. 2012 ; 19(10): 667-674) (Year: 2012).*

* cited by examiner

*Primary Examiner* — Manjunath N Rao
*Assistant Examiner* — Jae W Lee

(57) ABSTRACT

The present invention relates to a chimeric recombinant protein having a therapeutic effect on cervical cancer by fusing genetic modified E6 and E7, which are carcinogenesis-inducing proteins of human papillomavirus high-risk group type 16, with a fusion protein for increasing immunogenicity, the HPV type 16 E6, E7 chimeric recombinant protein fused with the flagellin fusion protein of the present invention showed the lowest tumor cell volume, and the immune response of specific T cells according to the recombinant antigen was significantly confirmed, and when the prophylactic effect was measured, it was confirmed that the volume of tumor cells was low and the antibody titer was increased, therefore human papillomavirus recombinant antigen of the present invention shows tumor treatment and prophylaxis and can be applied as a therapeutic/prophylactic vaccine composition.

11 Claims, 7 Drawing Sheets
Specification includes a Sequence Listing.

[Fig. 1]
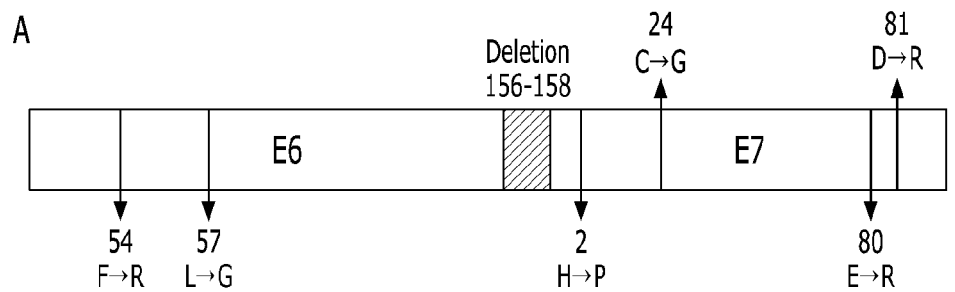
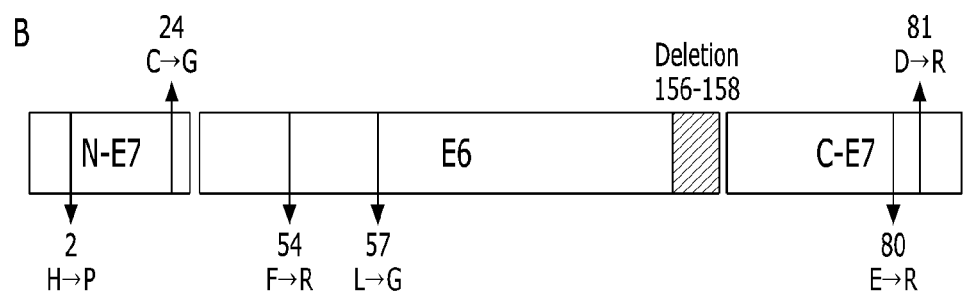
[Fig. 2]
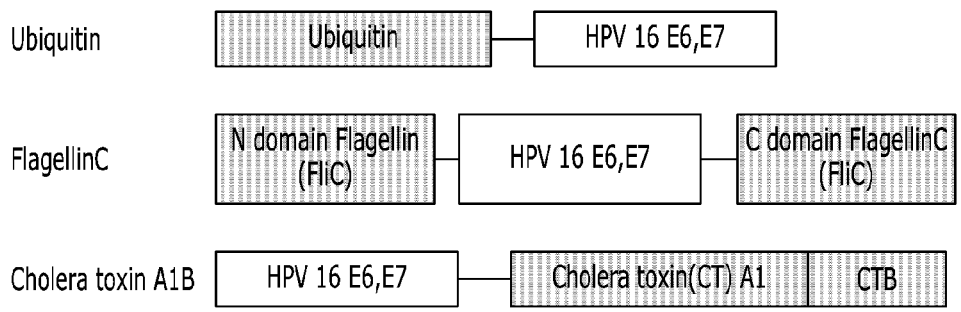

[Fig. 3]
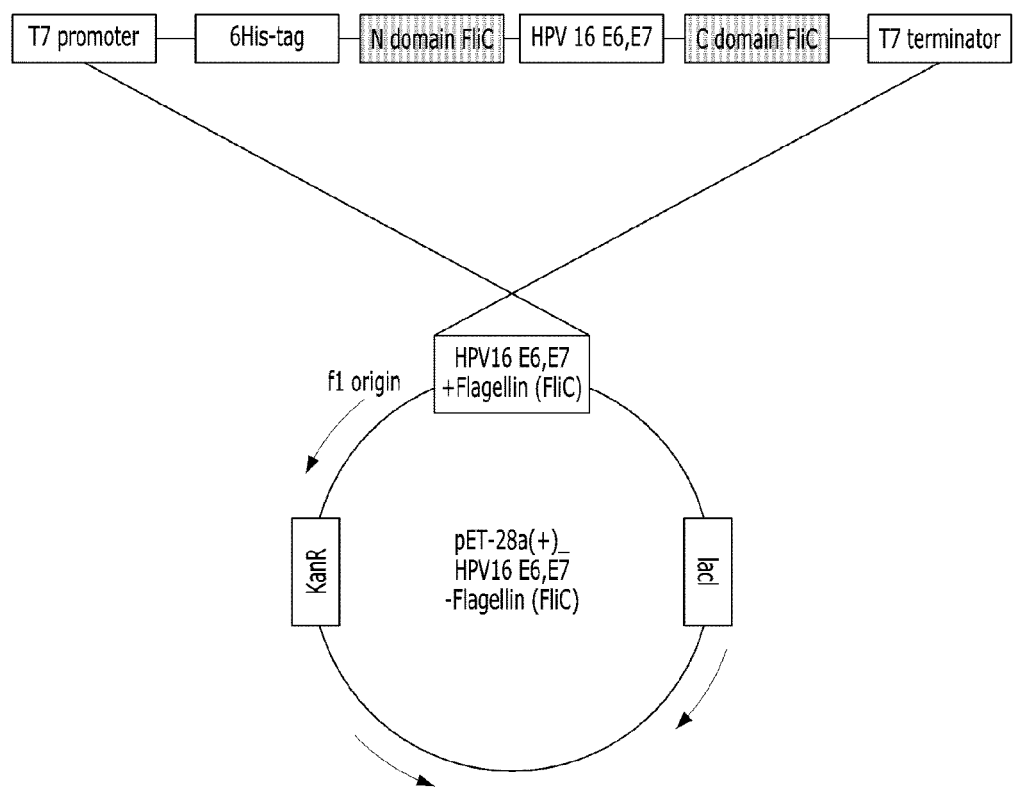

[Fig. 4]
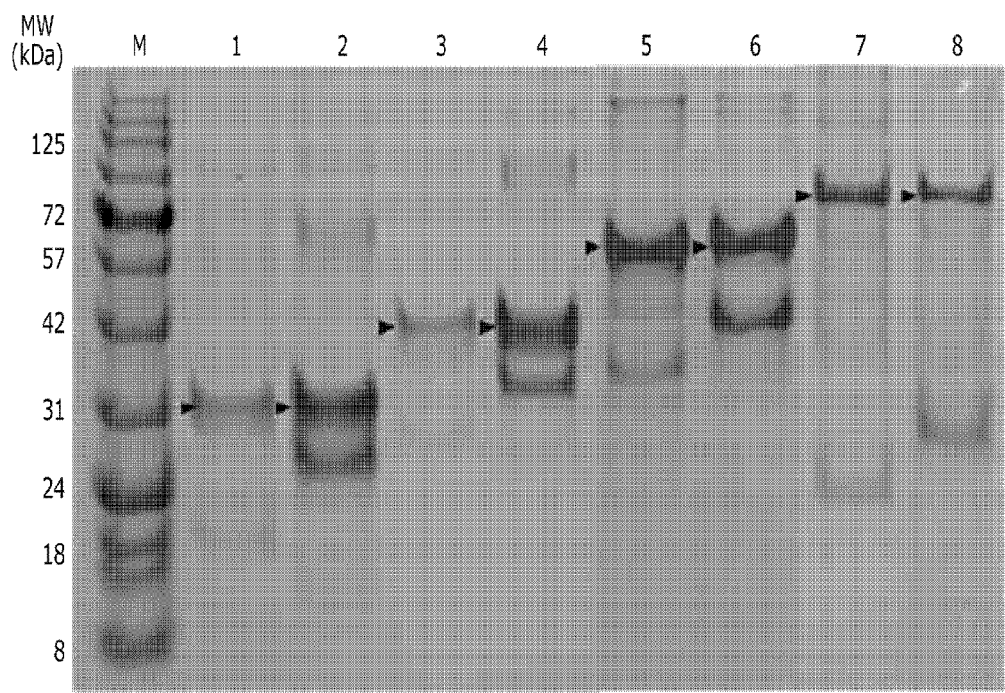
* M; size marker, Lane 1; Linear E6E7, Lane 2; Chimeric E6E7, Lane 3; Ubiquitin_linearE6E7, Lane 4; Ubiquitin_chimericE6E7, Lane 5; Flagellin (FliC)_linearE6E7, Lane 6; Flagellin (FliC)_chimericE6E7, Lane 7; Cholera toxinA1B_linear E6E7, Lane 8; Cholera toxinA1B_chimeric E6E7

[Fig. 5]
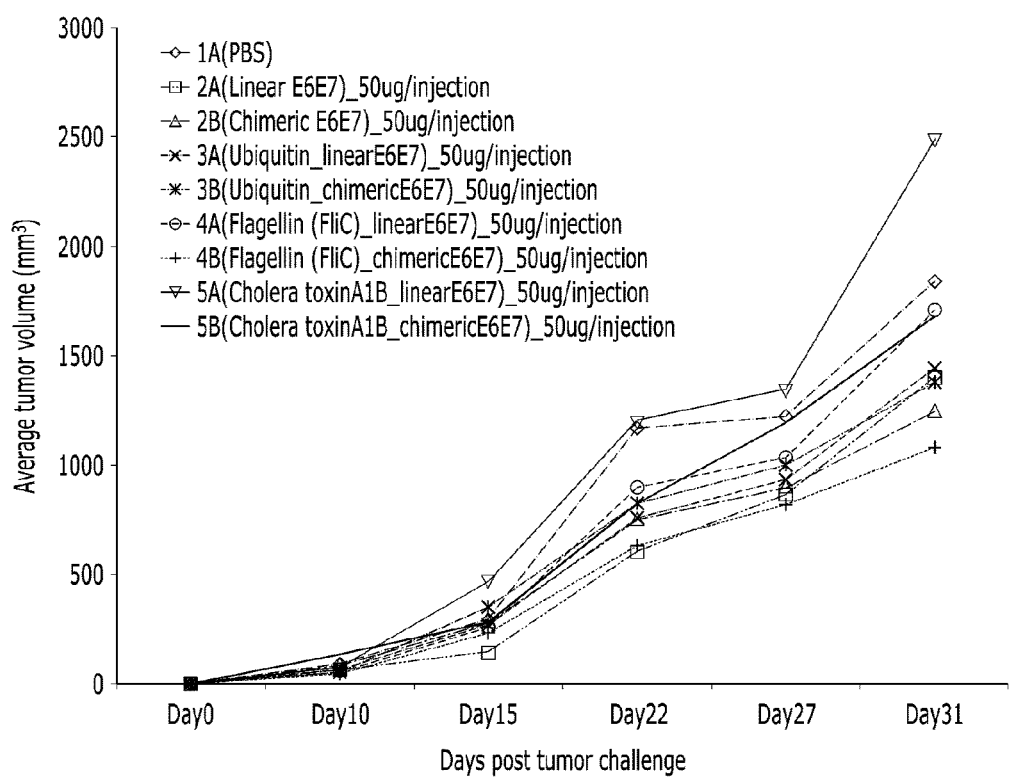

[Fig. 6]
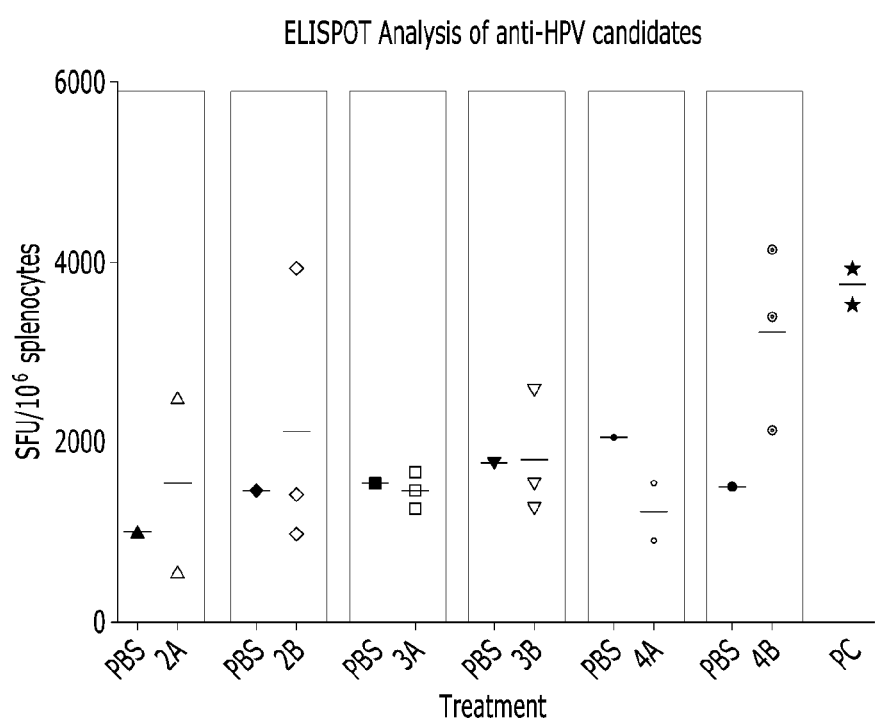
* 2A; Linear E6E7, 2B; Chimeric E6E7, 3A; Ubiquitin_linearE6E7, 3B; Ubiquitin_chimericE6E7, 4A; Flagellin (FliC)_linearE6E7, 4B; Flagellin (FliC)_chimericE6E7, PC; positive control

[Fig.7]
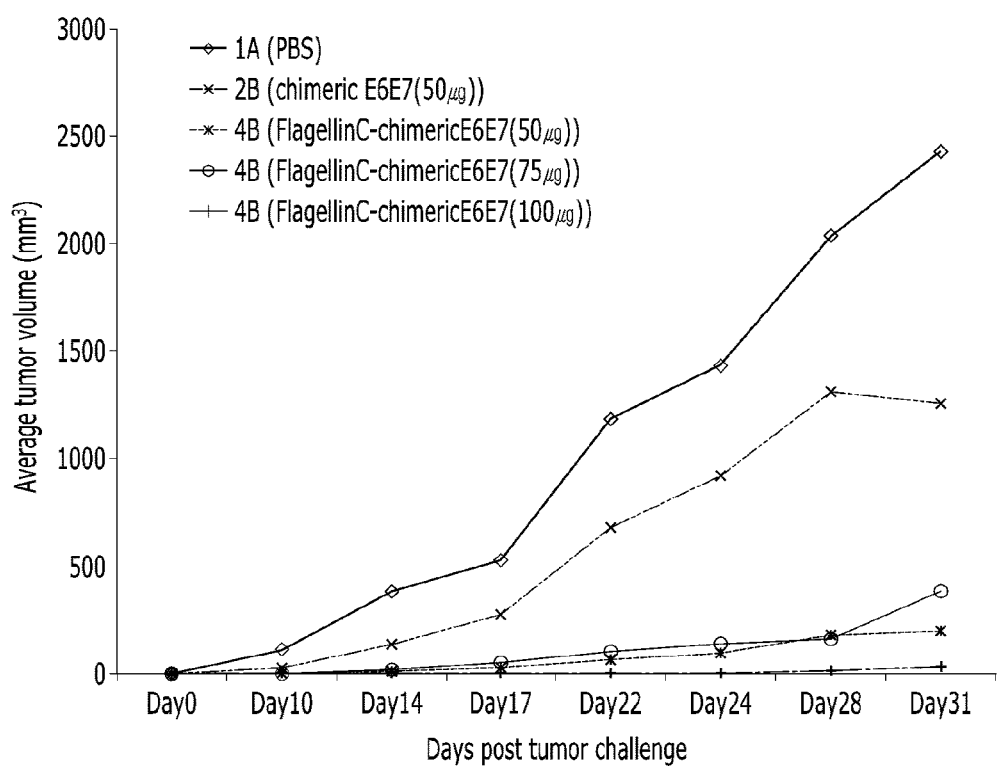

[Fig. 8]
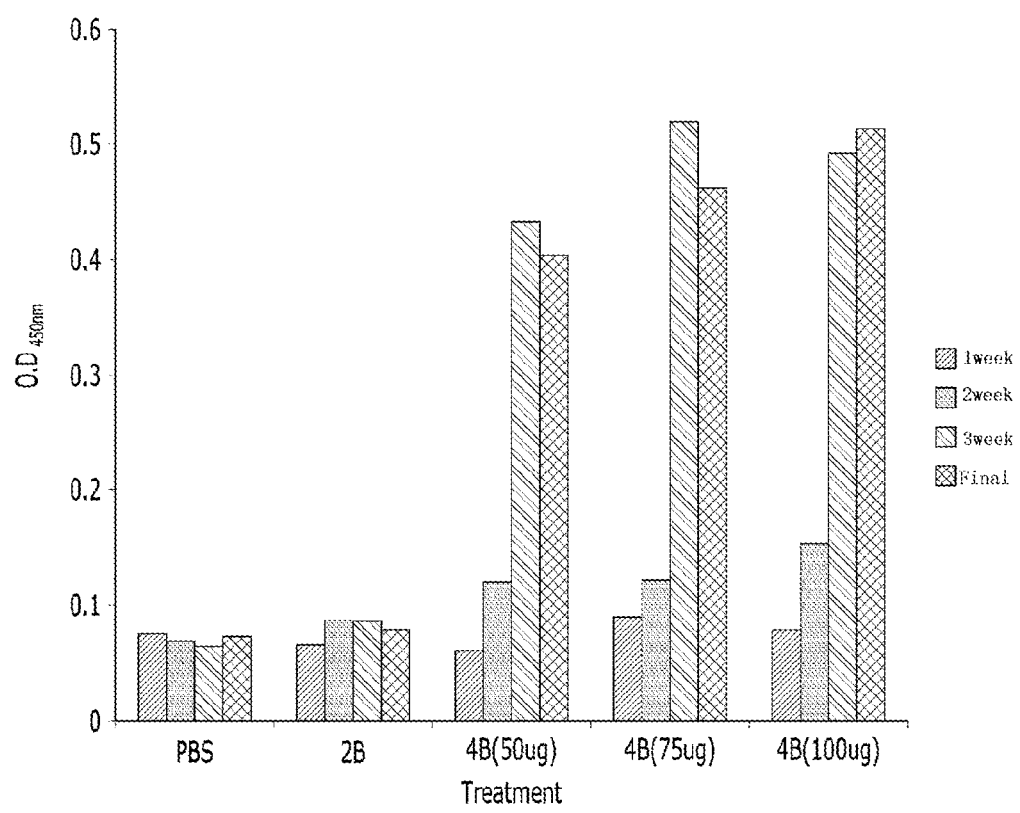
* 2B; Chimeric E6E7, 4B; Flagellin (FliC)_chimericE6E7

STRUCTURALLY MODIFIED CHIMERIC POLYPEPTIDE OF HUMAN PAPILLOMAVIRUS, RECOMBINANT PROTEIN COMPRISING SAME POLYPEPTIDE, AND USE OF SAME PROTEIN

TECHNICAL FIELD

The present invention relates to a therapeutic composition comprising a modified chimeric polypeptide of human papillomavirus (HPV) protein, a recombinant protein in which the polypeptide is combined with a fusion protein, and composition for treating cervical cancer using the recombinant protein. More specifically, induction of HPV type 16-specific immune response to HPV by including tertiary structurally modified chimeric recombinant protein to increase the expression amount and solubility of E6 and E7 recombinant protein of high risk group type 16 of human papillomavirus and a fusion protein for increasing immunogenicity suggests the possibility of a vaccine for the treatment/prevention of cervical cancer caused by HPV.

SEQUENCE LISTING

A Sequence Listing is provided herewith as a Sequence Listing, "OP21-0004HSUS_ST25" created on Nov. 8, 2022, and having a size of 14.3 KB. The contents of the Sequence Listing are incorporated by reference herein in their entirety.

BACKGROUND ART

Cancer is the leading cause of death worldwide, and human papillomavirus (HPV)—related cancers are estimated to account for 5% of all human cancers. HPV was identified as the leading cause of cervical cancer by Zur Hansen's group in the 1970s, and is the fourth most common cancer in women, with approximately 528,000 cases each year and 266,000 deaths.

There are about 170 HPV genotypes in HPV, and they are largely divided into high risk (hr) and low risk groups. Low-risk types of causing genital warts include HPV-6/11/40/42/43/44/54/61 and 72 types, and high-risk types include HPV-16/18/31/35/39/45/51/52/56/58/66 and 68 types, the high-risk types account for about 99.7% of cervical cancers.

In particular, HPV-16 and 18 types are the most common types associated with cervical cancer worldwide, accounting for more than 70% of cases. HPV is also the cause of many penile, vulvar, and anal related carcinomas and accounts for more than 40% of oropharyngeal cancers.

Persistent infection with such high-risk HPV causes the development of squamous intraepithelial lesions(SILs). This is called cervical intraepithelial neoplasia (CIN) in the cervix and vulva intraepithelial neoplasia (VIN) in the vulva, and these SILs can progress to malignant cancer.

HPV is a virus that has no envelope and consists of double-stranded DNA with a genome size of about 8 kb. The genome contains six early regulatory proteins (E1, E2, E4, E5, E6 and E7) and two late structural proteins (L1 and L2). Early genes encode proteins involved in viral DNA replication, transcription and oncogenic transformation, and late genes encode viral capsid proteins. In a typical high-risk HPV cancer formation process, the viral genome is integrated into the host's chromosomal DNA and the E2 genetic sequence is disrupted during the linearization of the gene. Since E2 protein is a transcriptional repressor of E6 and E7, when E2 is disrupted, expression of E6 and E7 proteins begins. E6 protein promotes the degradation of p53, a protein that regulates apoptosis in the host, and activates telomerase to prolong the lifespan of cells. In addition, E7 protein targets and degrades retinoblastoma protein (pRb), a tumor suppressor protein. As such, E6 and E7 interfere with cell cycle regulation and prolong the lifespan of host cells, leading to genetic instability, malignant transformation of cells, and cancer.

Currently, there are three commercially available HPV preventive vaccines: the bivalent (HPV-16/18) vaccine, Cervarix®, 4-valent (HPV-6/11/16/18) vaccine, Gardasil®, and the 9-valent (HPV-6/1811/16/18/31/33/45/52/58) vaccine, Gardasil®. These vaccines take advantage of the fact that the HPV L1 protein can be expressed to form virus-like particles (VLPs) that morphologically and antigenically closely resemble common viruses.

These three vaccines effectively prevent HPV infection caused by the target type by inducing the production of neutralizing antibodies that bind to viral particles and block entry into host cells.

However, since the antigen of these vaccines, the L1 capsid protein, is not expressed in already infected basal epithelial cells, these vaccines are not effective in clearing the pre-existing infection.

Therefore, people who have already been infected with HPV will not be able to benefit from these vaccines. In addition, developing countries have the biggest problem of HPV infection and malignancy due to the lack of resources to implement efficient vaccination and screening programs. In addition, the high cost of the vaccine prevents the vaccine from being vaccinated in low-income families, and although HPV vaccination programs have been implemented in 76 countries and territories around the world, only 1% of women in low- and middle-income countries are vaccinated by these programs. Therefore, it is the time for a broadly targeting oncogenic HPV type and an inexpensive therapeutic vaccine.

In HPV therapeutic vaccines, clearing of infection in cellular immunity is more important than humoral immune response. HPV E6, E7 oncoproteins are essential for the pathogenesis and maintenance of malignant tumors and are expressed in pre-malignant and invasive lesions but are absent in healthy cells.

Therefore, these oncoproteins (E6, E7) cannot avoid immune responses caused by mutations, and are ideal targets for the development of therapeutic vaccines against HPV infection and lesions. An ideal therapeutic vaccine could target the E6 and E7 proteins to induce a strong tumor-specific T cell type 1 and cytotoxic T lymphocyte (CTL) response to kill infectious and malignant cells.

There are currently no vaccines for the treatment of HPV approved for use in humans, and extensive research is underway into various types of vaccine candidates that are in clinical trials.

HPV therapeutic vaccines are being developed by various methods using live vectors, nucleic acids, proteins, and whole cells (live vectors, nucleic acids, proteins, whole cells). Among these methods, vaccines using subunit vaccine platforms are considered safer than live vector vaccines because they temporarily exist in host cells to reduce the potential for toxicity by using antigens delivered in peptide or whole protein form.

Among them, the protein-based vaccine has the advantages of safety, massive production and stability, and unlike the peptide-based vaccine, it contains the HLA epitope for all antigens, so it has the advantage of not being limited to MHC. However, they exhibit low immunogenicity and promote the antibody response as a T-cell response through presentation to the MHC II complex preferentially over MHC I.

Thus, antigens must be able to target dendritic cells (DCs) to increase immunogenicity and presentation on MHC I pathways and activation of CD8+ T cells. To this end, protein-based vaccines must be developed by generating a fusion protein or adding an adjuvant.

Several clinical trials are underway to test the efficacy of such therapeutic protein vaccines, and the most important aspect is to improve the immunogenicity and CD8+ T cell response of the protein vaccine.

Protein-based vaccines have advantages in safety, productivity, and stability, but preferential antibody response over cytotoxic T lymphocytes (CTLs) due to low immunogenicity and preferential presentation of MHC II complexes.

Therefore, it should be developed using a fusion protein and an adjuvant to increase immunogenicity. Fusion proteins for increasing immunogenicity include several other proteins such as Fms-like tyrosine kinase-3 ligand (Flt3L), N domain of calreticulin (NCRT), heat shock protein, adenylate cyclase (CyaA), Ubiquitin, Flagellin, Cholera toxin.

Among these, ubiquitin has been shown to enhance MHC-1 antigen presentation by increasing proteasome degradation by fusing ubiquitin to the N-terminus of the protein in several studies, and the adjuvant properties of cholera toxin have been described in several studies, and it is known to enhances the absorption of co-administered antigens by increasing the permeability of the intestinal epithelium, and induces enhanced antigen presentation by antigen presenting cells (APCs), and increase the formation of IgA in B cells.

In addition, flagellin is a structural component of flagella, mainly associated with gram-negative bacteria, with variable regions (D2, D3) and amino(N)-terminal and carboxy (C)-terminal conserved regions (D0 and D1 domains).

Flagellin has been identified in several studies as an agonist of the Toll-like receptor (TLR5) receptor, which is associated with inflammatory and innate immune activity. In addition, the fusion of flagellin as an adjuvant has the potential to produce a safe and promising vaccine, with some vaccines undergoing clinical trials. In a study by John T et al., it was reported that antigenic determinant-specific CD8+ T-cell responses were induced by promoting the processing of flagellin fusion antigens. Furthermore, it has been demonstrated that activation of the innate immune system can induce various effects on tumor growth in vivo in several experimental animal models.

In *Salmonella enterica*, in a process known as flagellar phase mutation, two genes encode flagellar antigens, and alternately express different flagellar filament proteins, FliC (phase 1 antigen) and FljB (phase 2 antigen). The FliC and FljB flagellin proteins have the same first 71 amino acids and the last 46 amino acids, but have different amino acids exposed in the middle and have distinct antigenicity. Hayashi F group showed that stimulation of TLR5 toll-like receptor by bacterial flagellin protein, including *Salmonella* FliC protein, resulted in the recruitment of nuclear factor NF-κ and stimulation of tumor necrosis factor alpha production. In addition, it was shown that most *Salmonella*-specific CD4+ T lymphocytes generated in response to *Salmonella* infection are represented by flagellin epitopes.

DISCLOSURE

Technical Problem

The present invention was developed in response to the above needs, and an object of the present invention is to provide a chimeric polypeptide and a gene encoding the same to enhance the immunogenicity comprising the tertiary structure modification of E6 and E7 of the high-risk group HPV 16 type and the fusion protein to treat/prevent diseases caused by HPV.

Another object of the present invention is to provide a recombinant protein comprising the chimeric polypeptide.

Another object of the present invention is to provide a recombinant vector expressing the recombinant protein, a host cell, and a production method comprising solubilization of the recombinant protein using the host cell.

Another object of the present invention is to provide a composition comprising the recombinant protein.

Technical Solution

To achieve the above object, the present invention provides a chimeric polypeptide in which the structures of E6 and E7 are modified, comprising residues from the $1^{st}$ to the $155^{th}$ of the E6 protein derived from human papillomavirus type 16, the $1^{st}$ to the $37^{th}$ amino acids of the E7 protein, and the $33^{rd}$ to the $98^{th}$ amino acid of the E7 protein derived from human papillomavirus type 16 wherein the E6 protein has substitution mutations at the $54^{th}$ and the $57^{th}$ amino acid residues and the E7 protein has substitution mutations at the $2^{nd}$, the $24^{th}$, the $80^{th}$ and the $81^{st}$ amino acid residues.

In one embodiment of the present invention, in the chimeric polypeptide, preferably the $54^{th}$ amino acid of the E6 protein is substituted from phenylalanine to arginine, and the $57^{th}$ amino acid is substituted from leucine to glycine but is not limited thereto.

In another embodiment of the present invention, in the chimeric polypeptide, preferably the $2^{nd}$ amino acid of the E7 protein is substituted from histidine to proline, the $24^{th}$ amino acid is substituted from cystine to glycine, and the $80^{th}$ amino acid is substituted from glutamate to arginine, and the $81^{st}$ amino acid is substituted from aspartate to arginine, but the present invention is not limited thereto.

In another embodiment of the present invention, the chimeric polypeptide comprising the modified structure of E6 and E7 preferably comprising the amino acid sequence set forth in SEQ ID NO: 1, but all mutants that achieve the desired effect of the present invention through mutations such as one or more substitutions, deletions, etc. in the corresponding sequence are also comprised in the scope of the present invention.

The present invention also provides a recombinant protein comprising the chimeric polypeptide of the present invention and a protein for enhancing immunity of the chimeric polypeptide.

In one embodiment of the present invention, the protein for enhancing immunity is preferably selected from the group of ubiquitin, flagellin, and cholera toxin A1B, More preferably, the flagellin protein comprises amino acid residues from the $1^{st}$ to the $143^{rd}$ and amino acid residues from $409^{th}$ to the $495^{th}$ More preferably, the cholera toxin A1B comprises the $19^{th}$ to the $212^{th}$ amino acid residues of the A1 subunit and the $22^{nd}$ to the $124^{th}$ amino acid residues of the B subunit, and has substitution mutations at the $81^{st}$, the $124^{t}$h and the $130^{th}$ amino acid residues of the A1 subunit but not limited thereto.

In one embodiment of the present invention, the recombinant protein preferably comprises the amino acid sequence set forth in SEQ ID NO: 5, but all mutants that achieve the desired effect of the present invention through mutations such as one or more substitutions, deletions, etc. in the corresponding sequence are also comprised in the scope of the present invention.

The present invention also provides a polynucleotide encoding the chimeric polypeptide of the present invention.

The present invention also provides a polynucleotide encoding a recombinant protein comprising the chimeric polypeptide of the present invention and a protein for enhancing immunity of the chimeric polypeptide.

The present invention also provides a recombinant expression vector comprising the polynucleotide of the present invention.

The present invention also provides a transformed cell transformed with the recombinant expression vector of the present invention.

The present invention also provides a method for expressing a protein comprising a recombinant protein using the transformed cell of the present invention.

The present invention also provides a method for solubilizing insoluble pellets produced by the method of the present invention.

The present invention also provides a method of using the recombinant protein obtained by the method of the present invention as an antigen in an animal model.

The present invention provides the efficacy of the treatment of mouse tumor cells using the recombinant protein produced by the above method.

The present invention provides efficacy against the immune response of specific T cells according to the recombinant antigen produced by the method.

The present invention provides the efficacy of preventing mouse tumor cells using the recombinant protein produced by the above method.

The present invention provides an antibody titer by the prophylactic effect of the recombinant antigen produced by the above method.

The present invention also provides a composition for treating and/or preventing a human papillomavirus-related disease comprising the chimeric polypeptide or recombinant protein of the present invention.

In one embodiment of the present invention, the human papillomavirus-related disease is preferably a cervical cancer disease but is not limited thereto.

Another immunogenic composition according to the present invention is a composition capable of eliciting a humoral immune response.

To enhance the ability of the immunogenic composition of the invention to elicit an immune response, it is preferable to mix the active ingredient with an adjuvant and/or a surfactant and/or an immune modulating substance (such as a cytokine or chemokine).

The adjuvant may include, for example, oily liposomes, such as Freund's adjuvants, which are generally used in the form of an emulsion having an aqueous phase, or water-insoluble inorganic salts such as aluminum hydroxide, zinc sulfate, colloidal iron hydroxide, calcium phosphate or calcium chloride.

The immunogenic composition according to the invention is preferably in particular for immunotherapy used for eliciting an immune response by preparing and/or increasing the immune response in the host. In particular, the immunogenic composition of the present invention can be used for prevention of initiation or maintenance of malignant transformation due to HPV infection of a host or for treatment of a patient suffering from malignant transformation due to HPV infection, in particular HPV-16 or HPV-18 infection.

Such immunotherapeutic compositions can be used for cancer immunotherapy for the treatment of uncontrolled cell proliferation causing tumors in the host, particularly for uterine cancer immunotherapy associated with HPV infection. Accordingly, the immunotherapeutic compositions of the present invention provide a means for the development of therapeutic vaccines particularly suitable for the treatment of malignant conditions resulting from oncovirus infection, comprising tumor conditions.

In the present invention, a term such as "treatment" includes the effect of the proteins disclosed herein that results in a beneficial effect on a patient receiving treatment, such effect is observed at the cellular level or at the clinical level, including improvement or amelioration of a patient's condition, or restoration of a state of health, as a result of treatment. When the malignant condition to be treated is uncontrolled cell proliferation or tumorigenesis or persistence, beneficial effects may include stabilizing or preferably preventing, stopping, or reversing uncontrolled tumor growth or regression of the tumor.

Compositions for treating a malignant condition as described above may comprise a dosage of the active ingredient, preferably in an amount of from about 1 to about 1000 μg, preferably from about 10 to about 500 μg of the recombinant protein. When the composition comprises a recombinant protein of the present invention as an active ingredient, the dosage may comprise from about 10 to about 100 μg, preferably about 50 μg, of the recombinant protein.

Depending on the condition of the patient to be treated, the composition may be administered once or several times, e.g., regularly at intervals of several days, e.g., at intervals of 5 to 10 days, locally at the level of symptoms. Alternatively, the composition may be administered systemically.

The present invention also relates to said recombinant protein or said polynucleotide or a vaccine composition comprising a vector comprising said polynucleotides and, if appropriate, a pharmaceutically acceptable vehicle, formulated for administration to particularly a mammalian host, preferably a human, for eliciting an immune response, including a cell-mediated immune response and/or a humoral response.

The present invention also relates to a pharmaceutical composition comprising a recombinant protein or polynucleotide or vector of the present invention and a pharmaceutically acceptable vehicle for preventing or treating HPV infection.

According to another embodiment, the pharmaceutical composition comprises a recombinant protein or polynucleotide or vector according to the present invention and a pharmaceutically acceptable vehicle for preventing or treating the initiation or maintenance of malignant transformation due to HPV infection in a host.

Hereinafter, the present invention will be described.

The present invention uses a chimeric recombinant protein, and the present invention provides a chimeric recombinant antigen by using anticancer inducing E6 and E7 of human papillomavirus type 16 as immune antigens, and using a fusion protein of ubiquitin, flagellin, or cholera toxin A1B to increase its immunogenicity.

The present invention may comprise polypeptides in the form of linear (Linear; E6E7) and chimeric (Chimeric; NE7-E6-CE7) forms in which amino acids of E6 and E7, which are oncoproteins derived from human papillomavirus type 16, are substituted, and deleted.

In the case of the chimeric peptide, it is a chimeric (E7NE6E7C) form different from the linear form of E6 and E7 proteins, taking into account the structural instability of the amino-terminal domain (N-terminal domain; CR1, CR2) of E7 and the carboxy-terminal domain (C-terminal domain, CR3), and at the same time to present an epitope to the MHC I (Major Histocompatibility Complex I) molecule (Karosiene, E et al., Immunogenetics, 64:177-186, 2012). In addition, the effect of the E6E7 junction site on the cellular immune response was minimized through prediction of binding force with MHC molecules and internal linker using the E6 and E7 protein's own sequence rather than a foreign sequence and to remove the cancer-inducing ability of recombinant E6E7 protein, mutations were induced by selecting residues beneficial in physical and chemical aspects such as protein stability and solubility through the tertiary structure of E6 and E7 of HPV.

In addition, through structural prediction of the chimeric polypeptide, stability in the production process, such as exposure to a water-soluble environment, of key amino acids constituting the structure of the therapeutic vaccine protein formulation was confirmed (Drozdetskiy, A et al., Nucleic Acids Res, 43:W389-W394, 2015).

A "chimeric protein" or "chimeric polypeptide" generally refers to a protein composed of a plurality of protein components and refers to a continuous polypeptide linked through a bond at the amino terminus (N terminus) and carboxy terminus (C terminus), respectively.

In the present invention, in the papillomavirus type 16-derived oncoproteins E6 and E7 polypeptide, a chimeric protein or polypeptide comprising an E6 polypeptide between the amino-terminal E7 polypeptide and the carboxy-terminal E7 polypeptide is referred to as a chimeric protein or polypeptide (Chimeric; NE7-E6-CE7).

The present invention may include a polypeptide comprising an amino-terminal domain (amino acids 1 to 143) and a carboxy-terminal domain (amino acids 409 to 495) except for the variable regions (D2, D3) of flagellin among the fusion proteins.

The present invention may include a polypeptide in which a chimeric protein is located between the amino-terminal domain and the carboxy-terminal domain of the fusion protein flagellin of the invention.

In the present invention, in the expression vector of the recombinant protein, a commercialized vector pET-28a vector was used, and a detailed description thereof will be omitted.

In addition, the present invention provides E. coli cells for transforming the recombinant vector. E. coli, which is a prokaryotic cell, is preferred as the cell used as the host cell in the present invention, and the BL21(DE3) strain for expression of the recombinant vector in the present invention is used, but the present invention is not limited thereto.

Upon induction of overexpression of the transformed E. coli cells, O.D600 was 0.5-0.6, after induction with 1 mM of IPTG, expression time were preferably set to 4 hours.

In the present invention, expression of the recombinant protein was confirmed in the insoluble pellet, and the insoluble pellet was separated from the obtained cells using a cell disruption solution BugBuster® (Novagen). The insoluble pellet provides a protein denaturation method using a denaturing solution of 8 M urea, Tris, sodium chloride, GSH, and GSSG.

The present invention also provides a method for obtaining a target protein for each pH using a purification buffer to which urea is added after binding the solubilized recombinant protein using a ProBond™ nickel resin.

The present invention also provides 48 kinds of the composition which sets the conditions for solubilization of the obtained denatured protein.

In an embodiment of the present invention, the composition for solubilizing the recombinant protein was confirmed to be suitable in a composition comprising Tris-HCl pH8.5 buffer and 0.5 M Arginine but is not limited thereto.

The present invention provides a chimeric recombinant protein in which the human papillomavirus produced by the above method and a fusion protein are fused as an antigen.

In the present invention, a total of eight recombinant protein antigens produced by the above method provide efficacy in treating mouse tumor cells.

In the present invention, to confirm the efficacy of the therapeutic effect of cervical cancer caused by human papillomavirus, TC-1 tumor cells and the produced recombinant antigen were injected. According to an embodiment of the present invention, the therapeutic efficacy was confirmed by measuring the tumor volume after injection of the recombinant antigen. As a result, the recombinant antigen of HPV type 16 chimera E6 and E7(NE7-E6-CE7) fused with flagellin of the present invention was confirmed to have therapeutic efficacy on tumor volume compared to the control group.

In addition, the present invention provides efficacy against the immune response of specific T cells to a total of 8 recombinant antigens produced by the above method.

ELISPOT (Enzyme-Linked ImmunoSpot) experimental technique was used to confirm the immune response efficacy of specific T cells to antigen produced in the present invention. In the present invention, tumor cells and antigen-injected mouse splenocytes were isolated and the immune response to each antigen was confirmed. As a result, it is considered that the immune response to the antigen is induced in the recombinant antigen of the HPV type 16 chimera E6 and E7 (NE7-E6-CE7) fused with flagellin as shown in the results of verifying the efficacy of the tumor cell treatment.

The present invention provides the efficacy of preventing mouse tumor cells against two types of antigens for which the best therapeutic effect was confirmed among a total of 8 types of recombinant proteins produced by the above method. In the present invention, to confirm the effect of preventing cervical cancer caused by human papillomavirus, the produced recombinant antigen and TC-1 tumor cells were injected. In the present invention, after injecting the recombinant antigen, the tumor cells were injected to confirm the preventive effect on the occurrence of cancer. As a result, the prophylactic effect on tumor volume was confirmed at various concentrations of the recombinant antigen of HPV type 16 chimera E6 and E7 (NE7-E6-CE7) fused with flagellin of the present invention compared to the control group.

In addition, the present invention provides antibody titers against two antigens having the highest therapeutic efficacy among a total of eight recombinant antigens produced by the above method.

An ELISA (Enzyme-Linked Immunosorbent Assay) test method was used to confirm the antibody titer against two antigens among a total of eight recombinant antigens produced in the present invention. A total of two times antigens were injected into mice and serum was separated to determine the antibody titer to each antigen. As a result, it was confirmed that the antibody titer was largely induced in the recombinant antigen of HPV type 16 chimera E6 and E7 (NE7-E6-CE7) fused with flagellin.

Advantageous Effects

As can be seen from the present invention, an antigen that increases immunogenicity can be produced by fusing the fusion protein with carcinogenesis-inducing proteins E6 and E7 of the HPV 16 type of the present invention. Through E6, E7 chimeric antigen with the modified tertiary structure of the HPV 16 type developed in the present invention, the expression level was higher in recombinant protein production than in the linear structure, and structurally more stable even at the stage of solubilization. In addition, to increase immunogenicity, three fusion protein candidates are fused and a total of 8 recombinant protein antigens are injected to see the effect of tumor treatment and prevention in mice, tumor cells and the antigen are injected to measure the tumor volume, and by verifying the immune response and antibody titer of specific T cells according to the recombinant antigen, it is thought to be applicable as a subunit recombinant therapeutic/prophylactic vaccine for HPV.

DESCRIPTION OF DRAWINGS

FIG. 1 is a schematic diagram showing the genetic modification sites encoding HPV16 E6 and E7 proteins. A is a schematic diagram of the linear structure of E6 and E7, which are carcinogenic proteins of the HPV16 type, and B is a schematic diagram of the chimeric structure of the E6 and E7 proteins.

FIG. 2 is a schematic diagram showing the fusion positions of HPV16 E6, E7 proteins and three candidate fusion proteins (ubiquitin, flagellin, cholera toxin A1B).

FIG. 3 is a schematic diagram showing the structure of expression vectors of E6 and E7 proteins and flagellin fusion proteins.

FIG. 4 is a result of confirming the size of the HPV16-E6E7 linear or HPV16-NE7-E6-CE7 chimera and the fusion protein or non-fusion protein using Coomassie blue staining method. M is molecular weight marker, 1 is non-fused HPV 16_E6-E7, 2 is non-fused HPV 16_NE7-E6-CE7, 3 is HPV 16_E6-E7 fused with ubiquitin, 4 is HPV 16_NE7-E6-CE7 fused with ubiquitin, 5 is HPV 16_E6-E7 fused with flagellin, 6 is HPV 16_NE7-E6-CE7 fused with flagellin, 7 is HPV 16_E6-E7 fused with cholera toxinA1B, 8 is HPV 16_NE7-E6-CE7 fused with cholera toxinA1B recombinant antigen.

FIG. 5 is the result of measuring the size of the tumor, after subcutaneously injecting the tumor cell line TC-1 cells into C57BL/6 mice, and then injecting each recombinant antigen to measure the size of the cancer over time, it was confirmed that the tumor volume was the lowest in the HPV 16_NE7-E6-CE7 fused with flagellin group.

FIG. 6 is an ELISPOT result showing a specific T cell immune response according to the HPV recombinant antigen, confirming that the antigen-dependent immune response was induced in HPV 16_NE7-E6-CE7 fused with flagellin.

FIG. 7 shows the results of measuring the size of the tumor according to the preventive effect by subcutaneously injecting TC-1 cells, a tumor cell line, after injecting two recombinant antigens into C57BL/6 mice, and a total of three concentrations (50 μg, 75 μg, 100 μg) of the HPV 16_NE7-E6-CE7 fused with flagellin group showed a low tumor volume.

FIG. 8 is an ELISA result, and it was confirmed that antibody titers were increased in all groups including HPV 16_NE7-E6-CE7 fused with flagellin by measuring antibody titers according to two recombinant antigens.

MODE FOR INVENTION

Hereinafter, the present invention will be described in more detail by the following examples. However, the following examples are described with the intention of illustrating the present invention, and the scope of the present invention is not to be construed as being limited by the following examples.

Example 1: Genetic Modification Encoding HPV E6 and E7 Proteins

For genetic modification of the anticancer-inducing protein of HPV type 16, in the case of the E6 protein, substitution mutations at residues 54 and 57, and deletion mutations at residues 156-158 were induced to inhibit the destabilization of the anticancer protein p53 and the interaction with the oncogenic protein due to the PDZ binding domain. In the case of E7 protein, substitution mutations at residues 2, 24, 80, and 81 were induced to strongly inhibit the interaction with pRb, the main target, and to suppress the transforming activity of E7 itself.

It included a polypeptide in a linear (E6E7) form in which amino acids of E6 and E7, which are oncogenic proteins derived from human papillomavirus type 16, were substituted, and deleted, and in addition, the sequence of SEQ ID NO: 1 comprising the same mutation as the linear polypeptide comprised a chimeric polypeptide. Specifically, it is a fusion protein in which amino acids 1 to 37 of the E7 protein, amino acids 1 to 155 of the E6 protein, and amino acids 33 to 98 of the E7 protein are linked in this order. (See FIG. 1)

Example 2: Gene Sequence and Genetic Modification of Fusion Protein

Among the fusion proteins, amino acids from 1 to 76 of the ubiquitin polypeptide sequence were used, and substitution mutation at residue 76 was induced to avoid cleavage by ubiquitin hydrolase. The two types of the genetically modified HPV 16 E6 and E7 polypeptides of FIG. 1 were bound to the carboxy terminus of ubiquitin. The flagellin polypeptide comprised amino acid sequences 1 to 143, the amino-terminal domain of the conserved region, and amino acids 409 to 495, the carboxy-terminal domain, of two types of genetically modified HPV 16 E6, E7 polypeptide was comprised between the amino-terminal domain and the carboxy-terminal domain of flagellin. In addition, in the polypeptide of cholera toxin A1B, polypeptides of A1 subunit (19-212 amino acids) and B subunit (22-124 amino acids) were included, and to reduce toxicity, substitution mutation at residue A1 subunit 81, 124, and 130 was induced, and two types of genetically modified HPV 16 E6 and E7 polypeptides were bound to the amino terminus of the A1 subunit of cholera toxin. (See FIG. 2)

Example 3: Gene Synthesis to be Used as a Non-Fusion/Fusion Protein with Genetically Modified HPV16 E6 and E7

Genes of oncoproteins E6 and E7 were modified, and synthetic genes encoding these proteins were obtained, and synthetic genes for three types of fusion proteins for immune enhancement were obtained. Each protein was codon-optimized for easy expression in *E. coli* by selecting a strain as shown in Table 1.

TABLE 1

| | Accession no. |
|---|---|
| HPV 16_E6-E7 (Linear form) | E6; NP_041325.1, E7; NP_041326.1 |
| HPV 16_NE7-E6-CE7 (Chimeric form) | E6; NP_041325.1, E7; NP_041326.1 |
| Ubiquitin, Ubi) | NP_003324.1 |
| Flagellin, FliC) | NP_460912.1 |
| Cholera toxin A1B, CTA1B) | CTA; NP_231100.1, CTB; NP_231099.1 |

Table 1 shows the genetic information of HPV16 type E6, E7 and fusion protein candidates.

Example 4: HPV16-E6E7-Non-Fusion/Fusion Protein Recombinant Protein Cloning

An attempt was made to express a recombinant protein derived from *Escherichia coli* by fusing a synthetic gene of HPV 16 type linear or chimeric with a synthetic gene of ubiquitin, flagellin, and cholera toxin A1B. To obtain the corresponding gene, first, in first cloning, the three fusion protein genes and the HPV 16 type linear or chimeric synthetic gene are fused to the fusion protein using the primary cloning restriction enzyme shown in Table 2 and T4 DNA ligase. In addition, PCR was performed to add a stop codon using the primers in Table 3 to obtain a non-fused form of DNA. After obtaining the target DNA in the non-fusion form and in the fusion form, the target DNA was subcloned into the expression vector pET-28a using the restriction enzymes used for secondary cloning in Table 2 and T4 DNA ligase. As shown in Table 4, a total of 8 recombinant proteins were cloned. In addition, a total of 8 vectors shown in Table 4 were transformed into the BL21 (DE3) strain using a medium comprising kanamycin, and then each strain was selected.

TABLE 2

| | Restriction enzymes used for primary cloning | Restriction enzymes used for secondary cloning |
|---|---|---|
| Non-fusion | — | NdeI, XhoI (NEB, USA) |
| Ubiquitin fusion | BamHI, PstI (Roche, Swiss) | NdeI, XhoI (NEB, USA) |
| flagellin fusion | BamHI, HindIII (Roche, Swiss) | NdeI, XhoI (NEB, USA) |
| Cholera toxin A1B fusion | MfeI, HindIII (Takara, Japan) | BamHI, XhoI (NEB, USA) |

Table 2 lists restriction enzymes used for cloning

TABLE 3

```
Forward Primer 1,
                                   SEQ ID NO: 7
CGACGCG CATATG ATGCATCAAAAACGCAC Forward Primer 1,
                                   SEQ ID NO: 8
GAACGCG CATATG ATGCCGGGCGACAC Forward Primer 1,
                                   SEQ ID NO: 9
CTCGC CTCGAG TTA CGGCTTCTGAGAGCAG
```

Table 3 shows primer sequences for stop codon insertion

TABLE 4

| pET-28a_HPV 16_E6-E7 (Linear form) | pET-28a_HPV 16_NE7-E6-CE7 (Chimeric form) |
|---|---|
| pET-28a_Ubi_HPV 16_E6-E7 | pET-28a_Ubi_HPV 16_ NE7-E6-CE7 |
| pET-28a_FliC_HPV 16_E6-E7 | pET-28a_FliC_HPV 16_ NE7-E6-CE7 |
| pET-28a_CTA1B_HPV 16_E6-E7 | pET-28a_CTA1B_HPV 16_ NE7-E6-CE7 |

Table 4 shows the types of recombinant protein cloning

Example 5: Expression of HPV16-E6E7-Non-Fusion/Fusion Protein-pET-BL21 Recombinant Protein To confirm the expression of a total of 8 recombinant proteins in Table 4, the selected strain expressed the protein through induction of IPTG (Isopropyl β-D-1-thiogalactopyranoside). When expressing the selected bacteria, the expression temperature, absorbance (OD600), the concentration of the expression induction substance IPTG, shaking culture conditions, expression time after induction, etc. are applied as experimental conditions. Through the condition test, the optimal conditions for expression were established for 4 hours in a shaking incubator (shaker) at 37° C. and 200 rpm using the inducer IPTG 1.0 mM in absorbance (OD600=0.5-0.6).

To confirm the expression of the recombinant protein in bacterial cells, 5 ml of cell lysis solution BugBuster® (Novagen) per 1 g of the cells was used for 20 minutes stirring at room temperature, and then protein extraction was performed, and overexpression patterns were confirmed at each position through 10% SDS-PAGE. All expressed recombinant proteins were identified in the insoluble pellet, not the soluble supernatant.

Example 6: Isolation of HPV16-E6E7-Non-Fusion/Fusion Protein-pET-BL21 Recombinant Protein Inclusion Body The recombinant protein expressed in the insoluble pellet was stirred with the cell lysis solution and the supernatant was removed by centrifugation, and the pellet was suspended with 50 mM Tris ((Tris-(hydroxymethyl) aminomethane) buffer in the same volume as the supernatant and was lysed with ultrasonication and centrifugation were repeated three times in total. The chaotropic denaturant 8 M urea (Urea), 2 mM reduced glutathione (GSH) and 1 mM oxidized glutathione disulfide (GSSG) were added to final insoluble pellet, and then the pellet was suspended and was ultrasonically lysed and stored at 4° C. for 16 hours to obtain a denatured protein through a protein denaturation step to release the tertiary structure of the protein.

Example 7: Purification of HPV16-E6E7-Non-Fusion/Fusion Protein-pET-BL21 Recombinant Protein For the purification of the obtained denatured protein, open column purification was performed using a combination of 6×His-tag recombinant protein and nitrilotriacetic acid (Ni-NTA). The supernatant was obtained through centrifugation of the denatured protein that had undergone the solubilization step before purification, and impurities were removed using a syringe filter. This supernatant was stirred at room temperature for 2 hours to bind to the 6× His-tag of the N-term end of the target recombinant protein using ProBond™ nickel resin (NOVEX). Buffers used for protein purification all included 8 M urea, and buffers comprising 20 mM sodium phosphate and 0.5 M sodium chloride were used. For the buffers used for washing, pH 7.8, pH 6.5, pH 5.9, and pH 5.5 were used, and for the buffer for protein eluting, pH 4.0, pH 3.5, and pH 3.0 were used.

During purification, 5 ml of ProBond™ nickel resin was added to the column and washed with distilled water. Then, a pH 7.8 buffer was poured into the washed resin at 5 times the volume of the resin. After the buffer was all removed, the denatured protein was loaded into the column, mixed with the resin, and then transferred to a 15 ml tube and stirred at room temperature for 2 hours. After stirring was finished, the resin-bound denatured protein was transferred back to the column, and the buffer is flowed in the order of pH 7.8, pH 6.5, pH 5.9, and pH 5.5. And finally, to elute the protein, the eluted protein was obtained by flowing the buffer in the order of pH 4.0, pH 3.5, and pH 3.0. To confirm the obtained protein, the eluted protein was confirmed through 10% SDS/PAGE.

Example 8: Solubilization Method of HPV16-E6E7-Non-Fusion/Fusion Protein-pET-BL21 Recombinant Protein To solubilize the denatured protein purified by the above method, 48 kinds of compositions as shown in Table 5 were tested. Purified protein denatured with 8 M urea was added to 1 ml of each composition in a 1/100 volume ratio and mixed, followed by reaction at 4° C. for 16 hours or more. After the reaction, a composition in which the formation of an insoluble precipitate was not confirmed even after centrifugation at 4° C. 16,000 g for 10 minutes or more was established as a solubilization method.

As shown in Table 5, it was confirmed that the composition range for solubilization of the recombinant protein was suitable for compositions Nos. 31-36 and 43-48 comprising Tris-HCl pH8.5 buffer and 0.5 M Arginine. Among them, the composition that can most suitably solubilize a total of 8 recombinant proteins was identified as composition 31 in Table 4, and this composition includes 50 mM Tris-HCl pH8.5, 2 mM GSH, 0.2 mM GSSG, 20 mM NaCl, 0.5 M Arginine. Eight kinds of eluted denatured proteins were added in a volume ratio of 1/20 through the solubilized composition identified in this way and mixed, followed by reaction at 4° C. for 16 hours or more (Cited Patent_KR20170103473A).

TABLE 5

| Buffer 50 mM | Arginine 0M | | | | | | Arginine 0.5M | | | | | | |
|---|---|---|---|---|---|---|---|---|---|---|---|---|---|
| HEPES (pH 7.5) | 1 | 2 | 3 | 4 | 5 | 6 | 7 | 8 | 9 | 10 | 11 | 12 | GSH/GSSG 2/0.2 mM |
| | 13 | 14 | 15 | 16 | 17 | 18 | 19 | 20 | 21 | 22 | 23 | 24 | GSH/GSSG 10/2 mM |
| Tris-HCl (pH 8.5) | 25 | 26 | 27 | 28 | 29 | 30 | 31 | 32 | 33 | 34 | 35 | 36 | GSH/GSSG 2/0.2 mM |
| | 37 | 38 | 39 | 40 | 41 | 42 | 43 | 44 | 45 | 46 | 47 | 48 | GSH/GSSG 10/2 mM |
| | MgCl2/CaCl2 0 mM | | | MgCl2/CaCl2 2 mM | | | MgCl2/CaCl2 0 mM | | | MgCl2/CaCl2 2 mM | | | |
| NaCl | 20 mM | 60 mM | 180 mM | 20 mM | 60 mM | 180 mM | 20 mM | 60 mM | 180 mM | 20 mM | 60 mM | 180 mM | NaCl |

Table 5 shows the composition of 48 kinds of solubilization buffer screening

Example 9: Obtaining Protein Through Dialysis and Concentration of HPV16-E6E7-Non-Fusion/Fusion Protein-pET-BL21

Since the composition comprising the solubilized protein includes the diluted target protein and various chemical compositions, it is difficult to use it as an antigen material. Therefore, the remaining chemical composition was removed by exchanging with the final buffer using a dialysis membrane. The final buffer solution used was a 10 mM carbonate pH9.8 buffer, and the dialysis solution was replaced every 1 hour to remove the residual chemical composition. Thereafter, a concentrated recombinant protein was obtained through a concentration process using a centrifugal-type Amicon® tube including a 10 kDa protein separation membrane. To confirm the finally obtained protein, the protein was confirmed through 10% SDS/PAGE (see FIG. 4).

Example 10: Immunological Validation of HPV16-E6E7-Non-Fusion/Fusion Protein-pET-BL21 Recombinant Antigen Western blot was performed for immunological verification of the final obtained 8 recombinant antigens. 5× loading dye was added to each recombinant protein, bathed at 100° C. for 15 minutes, and electrophoresed using 10% SDS/PAGE. After that, proteins were transferred to Immobilon-P PVDF membrane (Merck, Germany) using Mini Trans-Blot (Bio-Rad) at 100V for 1 hour and 30 minutes, and PVDF membrane was blocked by stirring in 5% skim milk solution for 1 hour. After blocking, repeated washing with stirring with TBST solution, diluted 1:800 mouse-derived anti-HPV16 E7 monoclonal antibody in 5% skim milk solution used for blocking, and stirring at 4 degrees for 16 hours to bind the antibody to the protein did it After repeated washing with agitation with TBST solution, the HRP-conjugated goat-derived anti-mouse immunoglobulin G secondary antibody was diluted 1:5000 in 5% skim milk solution and stirred at room temperature for 1 hour to react. This was repeatedly washed by stirring with a TBST solution, followed by color development using a DAB (3,3-diaminobenzidine) substrate.

A total of 8 recombinant protein antigens reacted antibody-specifically, with antigens 1 and 2 about 31.5 kDa, antigens 3 and 4 about 41.5 kDa, antigens 5 and 6 about 59 kDa, and antigens 7 and 8 about 67 kDa in size. of the protein was detected. Under the same experimental conditions, the band density was generally darker in the chimeric structure than in the HPV 16 type E6, E7 linear structure. As for the difference in the fusion protein, it was the most intense in the recombinant protein antigen fused with flagellin.

Example 11: Confirmation of Tumor Treatment Effect of HPV16-E6E7-Non-Fusion/Fusion Protein-pET-BL21 Recombinant Antigen To confirm the therapeutic effect of the recombinant protein antigen on cervical cancer, TC-1 tumor cells and $1 \times 10^5$ cells were subcutaneously injected into the flank of 6-week-old C57BL/6 female mice, and 6 mice were used in each group. Seven days after injection of TC-1 cells, each recombinant protein was injected subcutaneously in the vicinity of the tumor cells in an amount of 50 µg. On the $21^{st}$ day after tumor cell injection, 50 µg of recombinant protein was subcutaneously injected into the vicinity of tumor cells a second time. Tumor size was estimated in mice by measuring the longest (length) and shortest dimension (width) using digital calipers every 4-5 days. Tumor volume was calculated by the following equation: Tumor volume= (length×width$^2$)/2.

As a result of measuring the tumor volume through the recombinant protein as shown in FIG. 5, the HPV16 type E6 and E7 proteins showed a lower tumor volume in the chimeric structural group than in the linear structural group, and the lowest tumor volume was confirmed in the chimeric structural group including the flagellin fusion protein, compared to the control group. (See FIG. 5)

Example 12: ELISPOT; Specific T Cell Immune Response by HPV16-E6E7-Non-Fusion/Fusion Protein-pET-BL21 Recombinant Antigen On the 35th day from the day of TC-1 cell injection, spleens were harvested from 3 mice in each group. After crushing the spleen using a cell strainer (Falcon) product, the spleen cells were recovered, and the spleen cells were washed with PBS buffer. Thereafter, red blood cells were removed using red blood cell lysis buffer, and the number of cells was counted for use in the ELISPOT experiment. For this experiment, mouse IFN-gamma ELISpot kit of R&D system was used. Then, on a plate coated with mouse IFN-gamma monoclonal antibody, $2 \times 10^5$ cells, $4 \times 10^4$ cells of splenocytes recovered from each mouse and 10 µg of the recombinant protein antigen injected into each mouse were put together in each well, and in a 37° C., 5% $CO_2$ incubator for 16 hours incubation. After washing 4 times using 1× Wash buffer, 100 µl of IFN-gamma detection antibody to which biotin is bound was added, followed by incubation by stirring at room temperature for 2 hours. After incubation, washing was performed 4 times using 1× Wash buffer, 100 µl of streptavidin-AKP (alkaline phosphate) was added and incubated at room temperature for 2 hours. After washing 4 times using 1× Wash buffer, 100 ul of BCIP/NBT substrate was added and incubated for 45 minutes at room temperature. When color development by the reaction appeared, washed with sterile water and counted the number of colored spots.

As a result of measuring the specific T cell immune response to each recombinant protein antigen by ELISPOT, the group in which flagellin was fused to the HPV16 type E6, E7 protein chimeric form showed high results compared to the control group, confirming that a specific immune response to the antigen was induced (See FIG. 6).

Example 13: Confirmation of Tumor Prevention Effect of HPV16-E6E7-Non-Fusion/Fusion Protein-pET-BL21 Recombinant Antigen To confirm the cervical cancer prevention effect of the recombinant protein antigen, 6-week-old C57BL/6 female mice were used in each group. From the results of confirming the therapeutic effect of FIGS. 5 and 6, the two most excellent recombinant protein antigens were selected to confirm the preventive effect. First, 50 µg of control (PBS) and one non-fusion recombinant protein were injected, and in the case of one fusion recombinant protein, 50, 75, and 100 µg of antigen were injected subcutaneously twice (14 days and 28 days before tumor cell injection). On the 14th day of injection of control and recombinant protein, $1 \times 10^5$ cells were injected subcutaneously in the flank of TC-1 tumor cells, and the longest (length) and shortest dimensions (width) of the tumor cells were measured using a digital caliper every 4-5 days. was measured to estimate the tumor size of the mouse. Tumor volume was calculated by the following equation: Tumor volume=(length×width$^2$)/2.

As a result of measuring the tumor volume through the recombinant protein as shown in FIG. 7, compared to the non-fusion chimeric recombinant protein, the tumor volume was lower in the chimeric structural group including all concentrations of the flagellin fusion protein, and the lowest tumor volume was confirmed in the group injected with 100 µg of the flagellin fusion protein. (See FIG. 7)

Example 14: ELISA; Antibody Titer Confirmation by the Preventive Effect of HPV16-E6E7-Non-Fusion/Fusion Protein-pET-BL21 Recombinant Antigen Control and recombinant antigens were subcutaneously injected twice, and on days 1, 2, 3, and 4 from the first injection day, 6 mice in each group were anesthetized and blood was collected. The serum was obtained by centrifugation from the collected blood. In this experiment, each recombinant antigen was coated on an immune plate at 4° C. for 16 hours. Washing was performed three or more times using 1× Wash buffer, and blocking was performed at 37° C. for 1 hour using a blocking buffer to prevent non-specific binding of the antibody. After blocking, each separated serum was diluted 1:100 and reacted at 37° C. for 1 hour, washed 3 times or more using 1× Wash buffer, and then reacted with Goat anti-mouse IgG-HPR antibody at 37° C. for 1 hour. After washing 3 times using 1× Wash buffer, 50 µl of TMB substrate was added and reacted at room temperature for 20 minutes. After stopping the reaction with 2 M sulfuric acid, absorbance was measured at a wavelength of 450 nm.

As a result of measuring the antibody titer against each recombinant protein antigen by ELISA, there was no increase in titer of the non-fusion recombinant protein compared to the control group, but in all the groups injected with the flagellin fusion protein, it was confirmed that the antibody titer significantly increased at the 3rd and 4th weeks. (See FIG. 8)

```
[sequence information]
Human papillomavirus type 16, E6,
E7 modified amino acid sequence
(E6 underlined)
                            SEQ ID NO: 1
MPGDTPTLHEYMLDLQPETTDLYGYEQLNDSS

EEEDEMHQKRTAMFQDPQERPRKLPQLCTELQ

TTIHDIILECVYCKQQLLRREVYDFARRDGCI

VYRDGNPYAVCDKCLKFYSKISEYRHYCYSLY

GTTLEQQYNKPLCDLLIRCINCQKPLCPEEKQ

RHLDKKQRFHNIRGRWTGRCMSCCRSSRTRRE

EEEDEIDGPAGQAEPDRAHYNIVTFCCKCDST

LRLCVQSTHVDIRTLRRLLMGTLGIVCPICSQ

KP

Human papillomavirus type 16, E6,
E7 modified nucleic acid sequence
(E6 underlined)
                            SEQ ID NO: 2
ATG CCG GGC GAC ACG CCG ACC TTA

CAT GAG TAC ATG CTT GAT TTA CAG

CCG GAA ACG ACC GAT TTA TAC GGT

TAC GAA CAG TTG AAC GAC TCT AGC

GAG GAA GAA GAC GAG ATG CAT CAA

AAA CGC ACC GCC ATG TTC CAA GAT

CCG CAA GAA CGT CCG CGC AAA CTG

CCG CAG CTT TGC ACC GAG CTG CAA

ACT ACC ATT CAT GAC ATT ATC CTT

GAG TGC GTG TAC TGT AAA CAG CAA

TTA TTG CGT CGC GAA GTA TAC GAC

TTC GCG CGC CGT GAC GGT TGT ATT

GTG TAC CGT GAC GGT AAC CCG TAT

GCA GTC TGC GAC AAA TGC CTG AAG

TTT TAC AGC AAG ATA AGC GAG TAC

CGT CAT TAT TGT TAT TCT TTG TAT

GGC ACC ACC CTT GAG CAG CAG TAC

AAT AAG CCG CTT TGT GAT TTG TTG

ATC CGT TGC ATT AAT TGC CAG AAA

CCG TTG TGC CCG GAA GAA AAG CAG

CGC CAT TTA GAC AAG AAG CAG CGT

TTC CAT AAT ATT CGC GGG CGC TGG

ACC GGT CGT TGT ATG AGC TGT TGC

CGT TCT AGC CGC ACT CGT CGT GAA

GAG GAA GAA GAC GAG ATT GAC GGT

CCG GCA GGG CAG GCC GAG CCG GAT

CGC GCT CAT TAT AAT ATC GTG ACT

TTT TGT TGT AAG TGT GAT AGC ACC

CTT CGC CTT TGT GTG CAA AGC ACC

CAT GTT GAC ATT CGT ACT TTG CGC

CGC TTA TTA ATG GGC ACG CTT GGT

ATT GTG TGC CCG ATC TGC TCT CAG

AAG CCG

Salmonella typhimurium str. LT2,
Flagellin (FliC) modified amino
acid sequence
(Linker underlined, Arrow HPV 16
E6, E7 location)
                            SEQ ID NO: 3
MAQVINTNSLSLLTQNNLNKSQSALGTAIERL

SSGLRINSAKDDAAGQAIANRFTANIKGLTQA

SRNANDGISIAQTTEGALNEINNNLQRVRELA

VQSANSTNSQSDLDSIQAEITQRLNEIDRVSG

QTQFNGVKVLAQDNTGGGGSGGGGSGSGXLQK

IDAALAQVDTLRSDLGAVQNRFNSAITNLGNT

VNNLTSARSRIEDSDYATEVSNMSRAQILQQA

GTSVLAQANQVPQNVLSLLR

Salmonella typhimurium
str. LT2,
Flagellin (FliC) modified nucleic
acid
sequence (Linker underlined, Arrow
HPV 16 E6, E7 location)
                            SEQ ID NO: 4
ATG GCG CAG GTT ATT AAC ACC AAT

AGC TTA TCT TTG CTT ACC CAG AAT

AAC TTA AAC AAA TCT CAA AGC GCT

CTT GGG ACG GCA ATC GAG CGT TTA

TCT AGC GGG CTG CGC ATT AAT TCT

GCT AAA GAC GAC GCG GCA GGT CAA

GCA ATC GCC AAC CGT TTC ACG GCA

AAC ATT AAG GGC CTT ACC CAA GCC

AGC CGT AAT GCT AAC GAC GGG ATC

TCT ATC GCG CAG ACC ACC GAA GGC

GCT CTG AAC GAG ATC AAC AAC AAC

TTG CAG CGC GTT CGT GAG TTA GCG

GTG CAA TCT GCC AAC AGC ACG AAT
```

-continued

```
AGC CAA TCT GAC TTA GAC AGC ATC
CAG GCC GAG ATC ACC CAG CGT CTT
AAT GAA ATT GAT CGC GTA TCT GGC
CAG ACG CAA TTT AAC GGG GTC AAG
GTT CTT GCG CAA GAT AAT ACC GGT
GGC GGT GGT TCT GGT GGG GGC GGC
AGC GGA TCC GGC AAG CTT GGT GGG
GGC GGC AGC GGC GGT GGC GGT TCT
TTG CAG AAA ATT GAC GCG GCA CTT
GCG CAG GTC GAC ACC CTT CGC AGT
GAC CTG GGG GCA GTT CAG AAC CGC
TTT AAT TCT GCC ATT ACG AAC CTG
GGG AAC ACT GTG AAC AAC CTT ACG
TCT GCG CGC TCT CGC ATC GAG GAC
TCT GAT TAT GCA ACT GAA GTG AGC
AAT ATG AGC CGC GCC CAA ATC TTG
CAG CAG GCA GGC ACC AGC GTT CTT
GCC CAG GCA AAC CAA GTT CCG CAA
AAT GTC CTT TCT CTT CTT CGT
```

FliC. HPV16 E6, E7 modified amino acid sequence (E6 underlined)
SEQ ID NO: 5

```
MAQVINTNSLSLLTQNNLNKSQSALGTAIERL
SSGLRINSAKDDAAGQAIANRFTANIKGLTQA
SRNANDGISIAQTTEGALNEINNNLQRVRELA
VQSANSTNSQSDLDSIQAEITQRLNEIDRVSG
QTQFNGVKVLAQDNTGGGSGGGGSGSGGLQM
PGDTPTLHEYMLDLQPETTDLYGYEQLNDSSE
EEDEMHQKRTAMFQDPQERPRKLPQLCTELQT
TIHDIILECVYCKQQLLRREVYDFARRDGCIV
YRDGNPYAVCDKCLKFYSKISEYRHYCYSLYG
TTLEQQYNKPLCDLLIRCINCQKPLCPEEKQR
HLDKKQRFHNIRGRWTGRCMSCCRSSRTRREE
EEDEIDGPAGQAEPDRAHYNIVTFCCKCDSTL
RLCVQSTHVDIRTLRRLLMGTLGIVCPICSQK
PQLGGKLGGGSGGGGSLQKIDAALAQVDTLR
SDLGAVQNRFNSAITNLGNTVNNLTSARSRIE
DSDYATEVSNMSRAQILQQAGTSVLAQANQVP
QNVLSLLR
```

FliC. HPV16 E6, E7 modified nucleic acid sequence (E6 underlined)
SEQ ID NO: 6

```
ATG GCG CAG GTT ATT AAC ACC AAT
AGC TTA TCT TTG CTT ACC CAG AAT
AAC TTA AAC AAA TCT CAA AGC GCT
CTT GGG ACG GCA ATC GAG CGT TTA
TCT AGC GGG CTG CGC ATT AAT TCT
GCT AAA GAC GAC GCG GCA GGT CAA
GCA ATC GCC AAC CGT TTC ACG GCA
AAC ATT AAG GGC CTT ACC CAA GCC
AGC CGT AAT GCT AAC GAC GGG ATC
TCT ATC GCG CAG ACC ACC GAA GGC
GCT CTG AAC GAG ATC AAC AAC AAC
TTG CAG CGC GTT CGT GAG TTA GCG
GTG CAA TCT GCC AAC AGC ACG AAT
AGC CAA TCT GAC TTA GAC AGC ATC
CAG GCC GAG ATC ACC CAG CGT CTT
AAT GAA ATT GAT CGC GTA TCT GGC
CAG ACG CAA TTT AAC GGG GTC AAG
GTT CTT GCG CAA GAT AAT ACC GGT
GGC GGT GGT TCT GGT GGG GGC GGC
AGC GGA TCC GGC GGT CTG CAG ATG
CCG GGC GAC ACG CCG ACC TTA CAT
GAG TAC ATG CTT GAT TTA CAG CCG
GAA ACG ACC GAT TTA TAC GGT TAC
GAA CAG TTG AAC GAC TCT AGC GAG
GAA GAA GAC GAG ATG CAT CAA AAA
CGC ACC GCC ATG TTC CAA GAT CCG
CAA GAA CGT CCG CGC AAA CTG CCG
CAG CTT TGC ACC GAG CTG CAA ACT
ACC ATT CAT GAC ATT ATC CTT GAG
TGC GTG TAC TGT AAA CAG CAA TTA
TTG CGT CGC GAA GTA TAC GAC TTC
GCG CGC CGT GAC GGT TGT ATT GTG
TAC CGT GAC GGT AAC CCG TAT GCA
GTC TGC GAC AAA TGC CTG AAG TTT
TAC AGC AAG ATA AGC GAG TAC CGT
CAT TAT TGT TAT TCT TTG TAT GGC
ACC ACC CTT GAG CAG CAG TAC AAT
AAG CCG CTT TGT GAT TTG TTG ATC
```

-continued
```
CGT TGC ATT AAT TGC CAG AAA CCG
TTG TGC CCG GAA GAA AAG CAG CGC
CAT TTA GAC AAG AAG CAG CGT TTC
CAT AAT ATT CGC GGG CGC TGG ACC
GGT CGT TGT ATG AGC TGT TGC CGT
TCT AGC CGC ACT CGT CGT GAA GAG
GAA GAA GAC GAG ATT GAC GGT CCG
GCA GGG CAG GCC GAG CCG GAT CGC
GCT CAT TAT AAT ATC GTG ACT TTT
TGT TGT AAG TGT GAT AGC ACC CTT
CGC CTT TGT GTG CAA AGC ACC CAT
GTT GAC ATT CGT ACT TTG CGC CGC
TTA TTA ATG GGC ACG CTT GGT ATT
GTG TGC CCG ATC TGC TCT CAG AAG
```

-continued
```
CCG CAA TTG GGT GGC AAG CTT GGT
GGG GGC GGC AGC GGC GGT GGC GGT
TCT TTG CAG AAA ATT GAC GCG GCA
CTT GCG CAG GTC GAC ACC CTT CGC
AGT GAC CTG GGG GCA GTT CAG AAC
CGC TTT AAT TCT GCC ATT ACG AAC
CTG GGG AAC ACT GTG AAC AAC CTT
ACG TCT GCG CGC TCT CGC ATC GAG
GAC TCT GAT TAT GCA ACT GAA GTG
AGC AAT ATG AGC CGC GCC CAA ATC
TTG CAG CAG GCA GGC ACC AGC GTT
CTT GCC CAG GCA AAC CAA GTT CCG
CAA AAT GTC CTT TCT CTT CTT CGT
```

The invention claimed is:

1. A chimeric polypeptide comprising modified E6 and E7 proteins of human papillomavirus type 16 (HPV 16), wherein said chimeric polypeptide comprises
   [i] amino acid residues 1-155 of the E6 protein as set forth in amino acid residues 38-192 of SEQ ID NO: 1;
   [ii] amino acid residues 1-37 of the E7 protein as set forth in amino acid residues 1-37 of SEQ ID NO: 1; and
   [iii] amino acid residues 38-98 of the E7 protein as set forth in amino acid residues 198-253 of SEQ ID NO: 1;
   wherein the E6 protein comprises substitutions at positions F91 and L94 of SEQ ID NO: 1 to a different amino acid residue, which positions corresponds to positions F54 and L57 of the E6 protein, respectively; and wherein the E7 protein comprises substitutions at positions H2, C24, E240 and D241 of SEQ ID NO: 1 to a different amino acid residue, which corresponds to positions H2, C24, E80 and D81 of the E7 protein, respectively.

2. The chimeric polypeptide according to claim 1, wherein the substitutions of E6 protein are F91R and L94G of SEQ ID NO: 1, which corresponds to F54R and L57G of the E6 protein, respectively.

3. The chimeric polypeptide according to claim 1, the substitutions of E7 protein are H2P, C24G, E240R and D241R of SEQ ID NO: 1, which corresponds to H2P, C24G, E80R and D81R of the E7 protein, respectively.

4. The chimeric polypeptide according to claim 1, wherein the chimeric polypeptide comprises the amino acid sequence as set forth in SEQ ID NO: 1.

5. A recombinant protein comprising the chimeric polypeptide of claim 1 fused to a protein for enhancing immunity of the chimeric polypeptide.

6. The recombinant protein according to claim 5, wherein the protein for enhancing immunity is selected from the group consisting of ubiquitin, flagellin, and cholera toxin A1B.

7. The recombinant protein according to claim 5, wherein the recombinant protein comprises the amino acid sequence as set forth in SEQ ID NO: 5.

8. The chimeric polypeptide according to claim 2, wherein the chimeric polypeptide comprising the amino acid sequence as set forth in SEQ ID NO: 1.

9. The chimeric polypeptide according to claim 3, wherein the chimeric polypeptide comprising the amino acid sequence as set forth in SEQ ID NO: 1.

10. The recombinant protein according to claim 6, wherein the recombinant protein comprises the amino acid sequence as set forth in SEQ ID NO: 5.

11. A polynucleotide encoding the chimeric polypeptide of claim 1.

* * * * *

SEQUENCE LISTING

<160> NUMBER OF SEQ ID NOS: 9

<210> SEQ ID NO 1
<211> LENGTH: 258
<212> TYPE: PRT
<213> ORGANISM: Artificial Sequence
<220> FEATURE:
<223> OTHER INFORMATION: Chimera polypeptide

<400> SEQUENCE: 1

```
Met Pro Gly Asp Thr Pro Thr Leu His Glu Tyr Met Leu Asp Leu Gln
1               5                   10                  15

Pro Glu Thr Thr Asp Leu Tyr Gly Tyr Glu Gln Leu Asn Asp Ser Ser
            20                  25                  30

Glu Glu Glu Asp Glu Met His Gln Lys Arg Thr Ala Met Phe Gln Asp
        35                  40                  45

Pro Gln Glu Arg Pro Arg Lys Leu Pro Gln Leu Cys Thr Glu Leu Gln
    50                  55                  60

Thr Thr Ile His Asp Ile Ile Leu Glu Cys Val Tyr Cys Lys Gln Gln
65                  70                  75                  80

Leu Leu Arg Arg Glu Val Tyr Asp Phe Ala Arg Arg Asp Gly Cys Ile
                85                  90                  95

Val Tyr Arg Asp Gly Asn Pro Tyr Ala Val Cys Asp Lys Cys Leu Lys
            100                 105                 110

Phe Tyr Ser Lys Ile Ser Glu Tyr Arg His Tyr Cys Tyr Ser Leu Tyr
        115                 120                 125

Gly Thr Thr Leu Glu Gln Gln Tyr Asn Lys Pro Leu Cys Asp Leu Leu
    130                 135                 140

Ile Arg Cys Ile Asn Cys Gln Lys Pro Leu Cys Pro Glu Glu Lys Gln
145                 150                 155                 160

Arg His Leu Asp Lys Lys Gln Arg Phe His Asn Ile Arg Gly Arg Trp
                165                 170                 175

Thr Gly Arg Cys Met Ser Cys Cys Arg Ser Ser Arg Thr Arg Arg Glu
            180                 185                 190
```

Glu Glu Glu Asp Glu Ile Asp Gly Pro Ala Gly Gln Ala Glu Pro Asp
            195                 200                 205

```
Val Gln Ser Ala Asn Ser Thr Asn Ser Gln Ser Asp Leu Asp Ser Ile
            100                 105                 110

Gln Ala Glu Ile Thr Gln Arg Leu Asn Glu Ile Asp Arg Val Ser Gly
        115                 120                 125
Gln Thr Gln Phe Asn Gly Val Lys Val Leu Ala Gln Asp Asn Thr Gly
    130                 135                 140

Gly Gly Gly Ser Gly Gly Gly Gly Ser Gly Ser Gly Gly Lys Leu Gly
145                 150                 155                 160

Gly Gly Gly Ser Gly Gly Gly Gly Ser Leu Gln Lys Ile Asp Ala Ala
                165                 170                 175
Leu Ala Gln Val Asp Thr Leu Arg Ser Asp Leu Gly Ala Val Gln Asn
            180                 185                 190
Arg Phe Asn Ser Ala Ile Thr Asn Leu Gly Asn Thr Val Asn Asn Leu
        195                 200                 205
Thr Ser Ala Arg Ser Arg Ile Glu Asp Ser Asp Tyr Ala Thr Glu Val
    210                 215                 220

Ser Asn Met Ser Arg Ala Gln Ile Leu Gln Gln Ala Gly Thr Ser Val
225                 230                 235                 240
Leu Ala Gln Ala Asn Gln Val Pro Gln Asn Val Leu Ser Leu Leu Arg
                245                 250                 255

<210> SEQ ID NO 4
<211> LENGTH: 768
<212> TYPE: DNA
<213> ORGANISM: Artificial Sequence
<220> FEATURE:
<223> OTHER INFORMATION: polynucleotide encoding Salmonella typhimurium
      str. LT2, Flagellin (FliC) modified amino acid sequence

<400> SEQUENCE: 4
atggcgcagg ttattaacac caatagctta tctttgctta cccagaataa cttaaacaaa      60
tctcaaagcg ctcttgggac ggcaatcgag cgtttatcta gcgggctgcg cattaattct     120
gctaaagacg acgcggcagg tcaagcaatc gccaaccgtt tcacggcaaa cattaagggc     180
cttacccaag ccagccgtaa tgctaacgac gggatctcta tcgcgcagac caccgaaggc     240
gctctgaacg agatcaacaa caacttgcag cgcgttcgtg agttagcggt gcaatctgcc     300
aacagcacga atagccaatc tgacttagac agcatccagg ccgagatcac ccagcgtctt     360
aatgaaattg atcgcgtatc tggccagacg caatttaacg gggtcaaggt tcttgcgcaa     420
gataataccg gtggcggtgg ttctggtggg ggcggcagcg gatccggcgg taagcttggt     480
gggggcggca gcggcggtgg cggttctttg cagaaaattg acgcggcact tgcgcaggtc     540
gacacccttc gcagtgacct gggggcagtt cagaaccgct ttaattctgc cattacgaac     600
ctggggaaca ctgtgaacaa ccttacgtct gcgcgctctc gcatcgagga ctctgattat     660
gcaactgaag tgagcaatat gagccgcgcc caaatcttgc agcaggcagg caccagcgtt     720
cttgcccagg caaaccaagt tccgcaaaat gtcctttctc ttcttcgt                  768

<210> SEQ ID NO 5
<211> LENGTH: 520
<212> TYPE: PRT
<213> ORGANISM: Artificial Sequence
<220> FEATURE:
<223> OTHER INFORMATION: FliC. HPV16 E6, E7 modified amino acid sequence

<400> SEQUENCE: 5

Met Ala Gln Val Ile Asn Thr Asn Ser Leu Ser Leu Leu Thr Gln Asn
1               5                   10                  15
```

```
Asn Leu Asn Lys Ser Gln Ser Ala Leu Gly Thr Ala Ile Glu Arg Leu
            20                  25                  30

Ser Ser Gly Leu Arg Ile Asn Ser Ala Lys Asp Asp Ala Ala Gly Gln
        35                  40                  45

Ala Ile Ala Asn Arg Phe Thr Ala Asn Ile Lys Gly Leu Thr Gln Ala
50                  55                  60

Ser Arg Asn Ala Asn Asp Gly Ile Ser Ile Ala Gln Thr Thr Glu Gly
65                  70                  75                  80

Ala Leu Asn Glu Ile Asn Asn Leu Gln Arg Val Arg Glu Leu Ala
                85                  90                  95

Val Gln Ser Ala Asn Ser Thr Asn Ser Gln Ser Asp Leu Asp Ser Ile
                100                 105                 110

Gln Ala Glu Ile Thr Gln Arg Leu Asn Glu Ile Asp Arg Val Ser Gly
            115                 120                 125

Gln Thr Gln Phe Asn Gly Val Lys Val Leu Ala Gln Asp Asn Thr Gly
    130                 135                 140

Gly Gly Gly Ser Gly Gly Gly Gly Ser Gly Ser Gly Gly Leu Gln Met
145                 150                 155                 160

Pro Gly Asp Thr Pro Thr Leu His Glu Tyr Met Leu Asp Leu Gln Pro
                165                 170                 175

Glu Thr Thr Asp Leu Tyr Gly Tyr Glu Gln Leu Asn Asp Ser Ser Glu
            180                 185                 190

Glu Glu Asp Glu Met His Gln Lys Arg Thr Ala Met Phe Gln Asp Pro
    195                 200                 205

Gln Glu Arg Pro Arg Lys Leu Pro Gln Leu Cys Thr Glu Leu Gln Thr
    210                 215                 220

Thr Ile His Asp Ile Ile Leu Glu Cys Val Tyr Cys Lys Gln Gln Leu
225                 230                 235                 240

Leu Arg Arg Glu Val Tyr Asp Phe Ala Arg Arg Asp Gly Cys Ile Val
                245                 250                 255

Tyr Arg Asp Gly Asn Pro Tyr Ala Val Cys Asp Lys Cys Leu Lys Phe
            260                 265                 270

Tyr Ser Lys Ile Ser Glu Tyr Arg His Tyr Cys Tyr Ser Leu Tyr Gly
    275                 280                 285

Thr Thr Leu Glu Gln Gln Tyr Asn Lys Pro Leu Cys Asp Leu Leu Ile
    290                 295                 300

Arg Cys Ile Asn Cys Gln Lys Pro Leu Cys Pro Glu Glu Lys Gln Arg
305                 310                 315                 320

His Leu Asp Lys Lys Gln Arg Phe His Asn Ile Arg Gly Arg Trp Thr
                325                 330                 335

Gly Arg Cys Met Ser Cys Cys Arg Ser Ser Arg Thr Arg Arg Glu Glu
            340                 345                 350

Glu Glu Asp Glu Ile Asp Gly Pro Ala Gly Gln Ala Glu Pro Asp Arg
    355                 360                 365

Ala His Tyr Asn Ile Val Thr Phe Cys Cys Lys Cys Asp Ser Thr Leu
    370                 375                 380

Arg Leu Cys Val Gln Ser Thr His Val Asp Ile Arg Thr Leu Arg Arg
385                 390                 395                 400

Leu Leu Met Gly Thr Leu Gly Ile Val Cys Pro Ile Cys Ser Gln Lys
                405                 410                 415

Pro Gln Leu Gly Gly Lys Leu Gly Gly Gly Ser Gly Gly Gly Gly
            420                 425                 430
```

```
Ser Leu Gln Lys Ile Asp Ala Ala Leu Ala Gln Val Asp Thr Leu Arg
            435                 440                 445

Ser Asp Leu Gly Ala Val Gln Asn Arg Phe Asn Ser Ala Ile Thr Asn
        450                 455                 460

Leu Gly Asn Thr Val Asn Asn Leu Thr Ser Ala Arg Ser Arg Ile Glu
465                 470                 475                 480

Asp Ser Asp Tyr Ala Thr Glu Val Ser Asn Met Ser Arg Ala Gln Ile
                485                 490                 495

Leu Gln Gln Ala Gly Thr Ser Val Leu Ala Gln Ala Asn Gln Val Pro
            500                 505                 510

Gln Asn Val Leu Ser Leu Leu Arg
            515                 520

<210> SEQ ID NO 6
<211> LENGTH: 1560
<212> TYPE: DNA
<213> ORGANISM: Artificial Sequence
<220> FEATURE:
<223> OTHER INFORMATION: FliC. HPV16 E6, E7 modified nucleic acid
      sequence

<400> SEQUENCE: 6
atggcgcagg ttattaacac caatagctta tctttgctta cccagaataa cttaaacaaa      60
tctcaaagcg ctcttgggac ggcaatcgag cgtttatcta gcgggctgcg cattaattct     120
gctaaagacg acgcggcagg tcaagcaatc gccaaccgtt tcacggcaaa cattaagggc     180
cttacccaag ccagccgtaa tgctaacgac gggatctcta tcgcgcagac caccgaaggc     240
gctctgaacg agatcaacaa caacttgcag cgcgttcgtg agttagcggt gcaatctgcc     300
aacagcacga atagccaatc tgacttagac agcatccagg ccgagatcac ccagcgtctt     360
aatgaaattg atcgcgtatc tggccagacg caatttaacg gggtcaaggt tcttgcgcaa     420
gataatcccg tggcggtgg ttctggtggg gcggcagcg atccggcgg tctgcagatg       480 ccgggcgaca cgccgacctt acatgagtac atgcttgatt tacagccgga aacgaccgat     540
ttatacggtt acgaacagtt gaacgactct agcgaggaag aagacgagat gcatcaaaaa     600
cgcaccgcca tgttccaaga tccgcaagaa cgtccgcgca aactgccgca gctttgcacc     660
gagctgcaaa ctaccattca tgacattatc cttgagtgcg tgtactgtaa acagcaatta     720
ttgcgtcgcg aagtatacga cttcgcgcgc cgtgacggtt gtattgtgta ccgtgacggt     780
aacccgtatg cagtctgcga caaatgcctg aagttttaca gcaagataag cgagtaccgt     840
cattattgtt attctttgta tggcaccacc cttgagcagc agtacaataa gccgctttgt     900
gatttgttga tccgttgcat taattgccag aaaccgttgt gcccggaaga aaagcagcgc     960
catttagaca agaagcagcg tttccataat attcgcgggc gctggaccgg tcgttgtatg    1020
agctgttgcc gttctagccg cactcgtcgt gaagaggaag aagacgagat tgacggtccg    1080
gcagggcagg ccgagccgga tcgcgctcat tataatatcg tgactttttg ttgtaagtgt    1140
gatagcaccc ttcgcctttg tgtgcaaagc acccatgttg acattcgtac tttgcgccgc    1200
ttattaatgg gcacgcttgg tattgtgtgc ccgatctgct tcagaagcc gcaattgggt     1260 ggcaagcttg gtggggcgg cagcggcggt ggcggttctt gcagaaaat tgacgcggca     1320 cttgcgcagg tcgacaccct tcgcagtgac ctgggggcag ttcagaaccg cttaattct     1380 gccattacga acctggggaa cactgtgaac aaccttacgt ctgcgcgctc tcgcatcgag    1440
gactctgatt atgcaactga agtgagcaat atgagccgcg cccaaatctt gcagcaggca    1500
```

```
ggcaccagcg ttcttgccca ggcaaaccaa gttccgcaaa atgtcctttc tcttcttcgt    1560
```

```
<210> SEQ ID NO 7
<211> LENGTH: 30
<212> TYPE: DNA
<213> ORGANISM: Artificial Sequence
<220> FEATURE:
<223> OTHER INFORMATION: Forward primer

<400> SEQUENCE: 7
cgacgcgcat atgatgcatc aaaaacgcac                                       30

<210> SEQ ID NO 8
<211> LENGTH: 27
<212> TYPE: DNA
<213> ORGANISM: Artificial Sequence
<220> FEATURE:
<223> OTHER INFORMATION: Forward primer

<400> SEQUENCE: 8
gaacgcgcat atgatgccgg gcgacac                                          27

<210> SEQ ID NO 9
<211> LENGTH: 30
<212> TYPE: DNA
<213> ORGANISM: Artificial Sequence
<220> FEATURE:
<223> OTHER INFORMATION: Reverse primer

<400> SEQUENCE: 9
ctcgcctcga gttacggctt ctgagagcag                                       30
```